US010765316B2

(12) United States Patent
 An et al.

(10) Patent No.: US 10,765,316 B2
(45) Date of Patent: Sep. 8, 2020

(54) OPHTHALMIC INFORMATION PROCESSING SYSTEM, OPHTHALMIC INFORMATION PROCESSING METHOD, AND RECORDING MEDIUM

(71) Applicants: TOPCON CORPORATION, Itabashi-ku, Tokyo (JP); TOHOKU UNIVERSITY, Sendai-shi, Miyagi (JP); RIKEN, Wako-shi, Saitama (JP)

(72) Inventors: Guangzhou An, Tokyo (JP); Masahiro Akiba, Toda (JP); Toru Nakazawa, Sendai (JP); Kazuko Omodaka, Sendai (JP); Hideo Yokota, Wako (JP)

(73) Assignees: TOPCON CORPORATION, Itabashi-ku, Tokyo (JP); TOHOKU UNIVERSITY, Sendai-shi, Miyagi (JP); RIKEN, Wako-shi, Saitama (JP)

( * ) Notice: Subject to any disclaimer, the term of this patent is extended or adjusted under 35 U.S.C. 154(b) by 154 days.

(21) Appl. No.: 15/925,922

(22) Filed: Mar. 20, 2018

(65) Prior Publication Data

US 2018/0368679 A1 Dec. 27, 2018

(30) Foreign Application Priority Data

Jun. 27, 2017 (JP) .................. 2017-124825

(51) Int. Cl.
 *A61B 3/14* (2006.01)
 *A61B 3/00* (2006.01)
 (Continued)

(52) U.S. Cl.
 CPC .............. *A61B 3/14* (2013.01); *A61B 3/0025* (2013.01); *A61B 3/102* (2013.01); *A61B 3/1233* (2013.01);
 (Continued)

(58) Field of Classification Search
 CPC ......... A61B 3/14; A61B 3/1233; A61B 3/102; A61B 3/0025; G06T 7/0012;
 (Continued)

(56) References Cited

U.S. PATENT DOCUMENTS 6,134,341 A 10/2000 Kawamura et al.
9,700,210 B2 * 7/2017 Iwase ................... A61B 5/0066
 (Continued)

FOREIGN PATENT DOCUMENTS

JP H10-155744 A 6/1998
JP 2000-245700 A 9/2000
 (Continued)

OTHER PUBLICATIONS

Nicolela, et al.; "Various Glaucomatous Optic Nerve Appearances"; Ophthalmology, vol. 103, Issue 4, Apr. 1996; pp. 640-649.

*Primary Examiner* — Tuyen Tra
(74) *Attorney, Agent, or Firm* — Chiesa Shahinian & Giantomasi PC (57) ABSTRACT

An ophthalmic information processing system according to an embodiment includes a receiver and a processor. The receiver receives morphological data of an eye fundus of a subject. In addition, the receiver receives background data of the subject. The processor executes optic nerve head shape classification based on the morphological data and the background data received by the receiver.

14 Claims, 4 Drawing Sheets

(51) Int. Cl.
*A61B 3/10* (2006.01)
*A61B 3/12* (2006.01)
*G06T 7/00* (2017.01)

(52) U.S. Cl.
CPC .. *G06T 7/0012* (2013.01); *G06T 2207/10101* (2013.01); *G06T 2207/20084* (2013.01); *G06T 2207/30041* (2013.01)

(58) Field of Classification Search
CPC . G06T 2207/20084; G06T 2207/10101; G06T 2207/30041
USPC .......................................... 351/200, 205, 206
See application file for complete search history.

(56) References Cited

U.S. PATENT DOCUMENTS

| | | | |
|---|---|---|---|
| 10,149,610 B2* | 12/2018 | Narasimha-Iyer ... | A61B 3/0025 |
| 2007/0188705 A1 | 8/2007 | Tajima et al. | |
| 2010/0142852 A1 | 6/2010 | Fujita et al. | |
| 2015/0366452 A1 | 12/2015 | Iwase | |

FOREIGN PATENT DOCUMENTS

| | | | |
|---|---|---|---|
| JP | 2005-253796 A | 9/2005 | |
| JP | 2006-263127 A | 10/2006 | |
| JP | 2007-252707 A | 10/2007 | |
| JP | 2008-220617 A | 9/2008 | |
| JP | 2008-237839 A | 10/2008 | |
| JP | 2008-237840 A | 10/2008 | |
| JP | 2011-083555 A | 4/2011 | |
| JP | 2016-002380 A | 1/2016 | |
| JP | 2016-187475 A | 11/2016 | |

* cited by examiner

| No. | FEATURE AMOUNT | No. | FEATURE AMOUNT | No. | FEATURE AMOUNT |
|---|---|---|---|---|---|
| 1 | Sex | 32 | cpRNFLT (4 sec: Superior) | 63 | SkewT(T) |
| 2 | Age | 33 | cpRNFLT (4 sec: Nasal) | 64 | SkewI(T) |
| 3 | Spherical Equivalent | 34 | cpRNFLT (4 sec: Inferior) | 65 | SkewN(T) |
| 4 | Visual Field Test Mean Defect | 35 | Difference of cpRNFLT (4 sec: Superior and 4 sec: Inferior) | 66 | BOSALL(T) |
| 5 | Visual Field Test Pattern Standard Deviation | 36 | cpRNFLT (6 sec: Temporal) | 67 | BOSS(T) |
| 6 | Intraocular Pressure | 37 | cpRNFLT (6 sec: Temporal Superior) | 68 | BOST(T) |
| 7 | Central Corneal Thickness | 38 | cpRNFLT (6 sec: Nasal Superior) | 69 | BOSI(T) |
| 8 | Disc Area | 39 | cpRNFLT (6 sec: Nasal) | 70 | BOSN(T) |
| 9 | Cup Area | 40 | cpRNFLT (6 sec: Nasal Inferior) | 71 | BOTALL(T) |
| 10 | Rim Area | 41 | cpRNFLT (6 sec: Temporal Inferior) | 72 | BOTS(T) |
| 11 | Disc Diameter (Vertical) | 42 | Rim Decentering Ratio (cpRNFLT) | 73 | BOTT(T) |
| 12 | Disc Diameter (Horizontal) | 43 | Difference of cpRNFLT (6 sec: Temporal Superior and 6 sec: Temporal Inferior) | 74 | BOTI(T) |
| 13 | Cup/Disc Ratio (Vertical) | 44 | cpRNFLT (12 sec: Temporal) | 75 | BOTN(T) |
| 14 | Cup/Disc Ratio (Horizontal) | 45 | cpRNFLT (12 sec: Temporal Superior) | 76 | RRALL(T) |
| 15 | Cup/Disc Ratio (Area) | 46 | cpRNFLT (12 sec: Superior Temporal) | 77 | RRS(T) |
| 16 | Rim/Disc Ratio (Area) | 47 | cpRNFLT (12 sec: Superior) | 78 | RRT(T) |
| 17 | Max Cup Depth | 48 | cpRNFLT (12 sec: Superior Nasal) | 79 | RRI(T) |
| 18 | Avg Cup Depth | 49 | cpRNFLT (12 sec: Nasal Superior) | 80 | RRN(T) |
| 19 | Rim/Disc Average (Temporal) | 50 | cpRNFLT (12 sec: Nasal) | 81 | FAIALL(T) |
| 20 | Rim/Disc Average (Temporal Superior) | 51 | cpRNFLT (12 sec: Nasal Inferior) | 82 | FAIS(T) |
| 21 | Rim/Disc Average (Nasal Superior) | 52 | cpRNFLT (12 sec: Inferior Nasal) | 83 | FAIT(T) |
| 22 | Rim/Disc Average (Nasal) | 53 | cpRNFLT (12 sec: Inferior) | 84 | FAII(T) |
| 23 | Rim/Disc Average (Nasal Inferior) | 54 | cpRNFLT (12 sec: Inferior Temporal) | 85 | FAIN(T) |
| 24 | Rim/Disc Average (Temporal Inferior) | 55 | cpRNFLT (12 sec: Temporal Inferior) | 86 | ATIALL(T) |
| 25 | Rim Decentering Ratio (Area) | 56 | AveALL(T) | 87 | ATIS(T) |
| 26 | Disc Angle (Horizontal) | 57 | AveS(T) | 88 | ATIT(T) |
| 27 | Disc Height Difference | 58 | AveT(T) | 89 | ATII(T) |
| 28 | Max RPE Height Difference | 59 | AveI(T) | 90 | ATIN(T) |
| 29 | Disc Tilt Angle of Max RPE Height Difference | 60 | AveN(T) | 91 | Area Ratio of Blood Stream |
| 30 | cpRNFLT Average All | 61 | SkewALL(T) | | |
| 31 | cpRNFLT (4 sec: Temporal) | 62 | SkewS(T) | | |

| Confidence (SS) | 96.75 % |
|---|---|
| Confidence (FI) | 2.68 % |
| Confidence (MY) | 0.49 % |
| Confidence (GE) | 0.08 % |

OPHTHALMIC INFORMATION PROCESSING SYSTEM, OPHTHALMIC INFORMATION PROCESSING METHOD, AND RECORDING MEDIUM

CROSS-REFERENCE TO RELATED APPLICATIONS

This application claims priority to Japanese Patent Application No. 2017-124825, filed Jun. 27, 2017, which is herein incorporated by reference in its entirety.

FIELD

Embodiments described herein relate to a system, a method, and a recording medium for processing ophthalmic information.

BACKGROUND

Glaucoma is one of major eye diseases. Glaucoma is a group of progressive diseases which results in damage to the optic nerve and vision loss. Glaucoma is a multifactorial disease, and subdivision of disease conditions and individualization of treatment are desired. Therefore, various tests and examinations are utilized for diagnosis of glaucoma, such as intraocular pressure examination, corner angle examination, fundus examination (e.g., degree of cupping of optic nerve head, defect of retinal nerve fiber layer, presence or absence of optic nerve head hemorrhage, presence or absence of circumpapillary chorioretinal atrophy), visual field test, image analysis (e.g., optic nerve head shape analysis, layer thickness analysis, lamina cribrosa analysis).

There are classifications according to the shape of the optic nerve head (referred to as optic nerve head shape classification) as the classification methods of the pathology of glaucoma. Classification by Nicolela et al. (referred to as Nicolela's classification) is one of the representatives of such classifications. Nicolela's classification defines four types according to the shape of optic nerve head, namely, focal ischemia (FI) type, myopic (MY) type, senile sclerotic (SS) type, and generalized enlargement (GE) type. The focal ischemia (FI) type is a type in which a notch exists on a part of the rim and a local defect in the optic nerve fiber layer is observed. The focal ischemia (FI) type is often found in females and often accompanied by migraine and stroke. The myopic (MY) type is a type in which the optic nerve head is tilted and crescent shaped peripapillary chorioretinal atrophy (PPA) accompanied by temporal cupping is observed. The myopic (MY) type is often found in younger generation and often accompanied by myopia. The senile sclerotic (SS) type is a type in which the optic nerve head is of circular shape, cupping is shallow, and halo is observed around the optic nerve head. The senile sclerotic (SS) type is often found in the elderly and often accompanied by cardiovascular disorders. The generalized enlargement (GE) type is a type in which a large deep circular cupping is exhibited. The generalized enlargement (GE) type is often accompanied by high intraocular pressure.

Typically, a doctor performs optic nerve head shape classification by interpreting a fundus image acquired using a retinal camera or a scanning laser microscope (SLO). In other words, the classification is performed by the subjectivity of the doctor. Meanwhile, automation of the classification is desired in view of the relatively high prevalence rate of glaucoma and the importance of early detection.

However, the image quality of fundus images obtained by retinal cameras or SLOs is greatly affected by photographing conditions etc. Therefore, quantification of optic nerve head shape parameters is difficult, which is one of the factors that prevents the automation of the classification.

The conventional classification refers only to fundus images (i.e., refers only to the optic nerve head shape parameters) and thus, it is difficult to perform classification with favorable accuracy and precision. On the other hand, although various kinds of ophthalmic information to be referred to is available for classification, considering all of them makes the processing complicated and enormous and the scale and resources of the processing system extremely large. Therefore, putting it into practice is supposed to be difficult.

The followings are examples of publications that disclose related conventional techniques: Japanese Unexamined Patent Application Publication No. Hei10-155744; Japanese Unexamined Patent Application Publication No. 2000-245700; Japanese Unexamined Patent Application Publication No. 2005-253796; Japanese Unexamined Patent Application Publication No. 2006-263127; Japanese Unexamined Patent Application Publication No. 2007-252707; Japanese Unexamined Patent Application Publication No. 2008-220617; Japanese Unexamined Patent Application Publication No. 2008-237839; Japanese Unexamined Patent Application Publication No. 2008-237840; Japanese Unexamined Patent Application Publication No. 2011-83555; Japanese Unexamined Patent Application Publication No. 2016-2380; Japanese Unexamined Patent Application Publication No. 2016-187475; and, Nicolela M T, Drance S M, "Various glaucomatous optic nerve appearances: clinical correlations", Ophthalmology, Volume 103, Issue 4, April 1996, Pages 640-649

BRIEF DESCRIPTION OF THE DRAWINGS

FIG. 2 is an example of a list of parameters applicable to the ophthalmic information processing system according to the exemplary embodiment.

DETAILED DESCRIPTION

Exemplary embodiments are described below.

The first aspect of an ophthalmic information processing system according to an exemplary embodiment may include a receiver and a processor. The receiver is configured to receive morphological data of an eye fundus of a subject and background data of the subject. The processor is configured to execute optic nerve head shape classification based on the morphological data and the background data.

The second aspect of the ophthalmic information processing system according to the exemplary embodiment is the ophthalmic information processing system of the first aspect and further includes a storage that pre-stores learning information generated by learning based on the same type of data group as the morphological data and the same type of data group as the background data. In addition, the processor of the second aspect executes the optic nerve head shape classification based on the learning information, the morphological data and the background data.

The third aspect of the ophthalmic information processing system according to the exemplary embodiment is the ophthalmic information processing system of the second aspect, wherein the morphological data of the third aspect includes at least one of the following parameters: cupping area; average cupping depth; maximum cupping depth; nasal rim-to-disc area ratio; horizontal disc angle; superior nasal circumpapillary retinal nerve fiber layer average thickness; and superior circumpapillary retinal nerve fiber layer average thickness. In addition, the background data of the third aspect includes at least one of age and spherical equivalent. Further, the learning information of the third aspect includes a classification model generated by learning using an artificial neural network ("neural network" for short). In addition, the processor of the third aspect includes a neural network classifier.

The fourth aspect of the ophthalmic information processing system according to the exemplary embodiment is the ophthalmic information processing system of the second aspect, wherein the morphological data of the fourth aspect includes at least one of the following parameters: horizontal disc angle; nasal rim-to-disc area ratio; average cupping depth; cup-to-disc area ratio; and superior nasal circumpapillary retinal nerve fiber layer average thickness. In addition, the background data of the fourth aspect includes at least one of age and spherical equivalent. Further, the learning information of the fourth aspect includes a classification model generated by learning using a gradient boosting decision tree. In addition, the processor of the fourth aspect includes a gradient boosting decision tree classifier.

The fifth aspect of the ophthalmic information processing system according to the exemplary embodiment is the ophthalmic information processing system of the second aspect, wherein the morphological data of the fifth aspect includes at least one of the following parameters: horizontal disc diameter; average cupping depth; nasal rim-to-disc area ratio; horizontal disc angle; superior nasal circumpapillary retinal nerve fiber layer average thickness; superior circumpapillary retinal nerve fiber layer average thickness; and disc retinal pigment epithelium height difference. In addition, the background data of the fifth aspect includes at least one of age and spherical equivalent. Further, the learning information of the fifth aspect includes a classification model generated by learning using a support vector machine. In addition, the processor of the fifth aspect includes a support vector machine classifier.

The sixth aspect of the ophthalmic information processing system according to the exemplary embodiment is the ophthalmic information processing system of the second aspect, wherein the morphological data of the sixth aspect includes at least one of the following parameters: superior circumpapillary retinal nerve fiber layer average thickness; nasal rim-to-disc area ratio; horizontal disc angle; and average cupping depth. In addition, the background data of the sixth aspect includes at least one of age and spherical equivalent. Further, the learning information of the sixth aspect includes a classification model generated by learning using Bayes. In addition, the processor of the sixth aspect includes a Bayes classifier.

The seventh aspect of the ophthalmic information processing system according to the exemplary embodiment is the ophthalmic information processing system of any of the second to sixth aspects and further includes a learner. The learner is configured to execute learning based on the same type of data group as the morphological data and the same type of data group as the background data to generate the learning information.

The eighth aspect of the ophthalmic information processing system according to the exemplary embodiment is the ophthalmic information processing system of any of the first to seventh aspects, wherein the processor of the eighth aspect is configured to execute the optic nerve head shape classification to determine confidence (certainty factor) for each of one or more types of optic nerve head shape. In addition, the system of the eighth aspect further includes a display controller that displays the confidence of the one or more types on a display device.

The ninth aspect of the ophthalmic information processing system according to the exemplary embodiment is the ophthalmic information processing system of any of the first to seventh aspects, wherein at least part of the morphological data of the ninth aspect is generated by analyzing data of the eye fundus acquired using optical coherence tomography.

The tenth aspect of the ophthalmic information processing system according to the exemplary embodiment is the ophthalmic information processing system of the ninth aspect and further includes an analysis processor that analyzes data of an eye fundus acquired using optical coherence tomography to generate morphological data.

The eleventh aspect of the ophthalmic information processing system according to the exemplary embodiment is the ophthalmic information processing system of the tenth aspect and further includes an optical coherence tomography apparatus that acquires data of an eye fundus using optical coherence tomography.

The twelfth aspect of the ophthalmic information processing system according to the exemplary embodiment is the ophthalmic information processing system of any of the first to eleventh aspects, wherein the receiver of the twelfth aspect is configured to receive at least part of the background data directly or indirectly from an electronic medical record system.

The first aspect of an ophthalmic information processing method according to an exemplary embodiment is a method of processing ophthalmic information executed by a computer, wherein the computer receives morphological data of an eye fundus of a subject and background data of the subject, and the computer executes optic nerve head shape classification based on the morphological data and the background data.

The second to twelfth aspects of the ophthalmic information processing method according to the exemplary embodiment include the processes according to the second to twelfth aspects of the ophthalmic information processing system according to the exemplary embodiment, respectively.

The first to twelfth aspects of the program according to the exemplary embodiment may be programs that cause a computer to execute the ophthalmic information processing method of the first to twelfth aspects, respectively.

The first to twelfth aspects of a recording medium according to the exemplary embodiment may be a non-transitory computer-readable recording medium storing programs of the first to twelfth aspects, respectively.

In an exemplary embodiment, any item related to the ophthalmic information processing system can be applied to any one or more of the ophthalmic information processing method, the program, and the recording medium. For example, any one or more aspects of the ophthalmic information processing system can be combined with any of the first aspect of the ophthalmic information processing method, the first aspect of the program, and the first aspect of the recording medium.

According to the exemplary embodiments, a technique for automatic execution of optic nerve head shape classification with favorable accuracy and precision can be achieved. In addition, according to these exemplary embodiments, a technique for automatic execution of optic nerve head shape classification with favorable accuracy and precision can be realized without using a large-scale system.

Hereinafter, an ophthalmic information processing system, an ophthalmic information processing method, a program, and a recording medium according to an exemplary embodiment will be described in detail with referring to drawings. An exemplary ophthalmic information processing method can be realized with an exemplary ophthalmic information processing system. An exemplary ophthalmic information processing system may include two or more apparatuses capable of communicating with each other (e.g., one or more computers, one or more storage devices, etc.). Alternatively, an exemplary ophthalmic information processing system may be a single apparatus (e.g., a computer including a storage device).

The hardware and software for realizing the exemplary ophthalmic information processing method is not limited to the ophthalmic information processing system exemplified below. The hardware and software may include a combination of any hardware and any software which contribute to realization of the exemplary ophthalmic information processing method. As a typical example, the ophthalmic information processing system may include hardware and software that functions as an artificial intelligent engine.

An exemplary ophthalmic information processing method is used to perform medical examinations. More specifically, the exemplary ophthalmic information processing method is used to process ophthalmic information for automatically classifying the shapes of optic nerve heads. In optic nerve head classification, morphological data of the eye fundus of a subject and background data of the subject are utilized.

The fundus morphological data represents the morphology (i.e., shape, size, etc.) of a fundus. The fundus morphological data is related to parameters of types selected from various kinds of ophthalmic information. Typically, the selection of the parameters is executed using a computer such as artificial intelligence. Alternatively, the selection of the parameters may be performed by an expert such as a doctor. Instead, both parameters selected by a computer and parameters selected by an expert may be taken into account. Specific examples of the types of the fundus morphological data and specific examples of the selection processing of the parameters will be described later.

The background data is data related to the subject and typically includes data acquired by methods other than medical examinations. The background data may include information recorded in (or associated with) an electronic medical record or the like. For example, an electronic medical record may include examination data acquired by a medical examination in addition to patient information (e.g., age and sex) acquired by a method other than medical examinations. Examples of the examination data include a visual acuity value, a refractive power value, a spherical equivalent, an intraocular pressure value, a corneal thickness value, a result of visual field test (e.g., mean defect value, pattern standard deviation value, etc.). The background data is related to parameters of types selected from various kinds of information. As in the case of the fundus morphological data, the selection of the parameters may be performed by at least one of a computer and an expert.

An exemplary program makes a computer, such as an exemplary ophthalmic information processing system, to execute an exemplary ophthalmic information processing method. In addition, an exemplary recording medium is a computer readable recording medium and records an exemplary program. The exemplary recording medium is a non-transitory recording medium. The exemplary recording medium may be an electronic medium utilizing magnetism, light, photomagnetism, of semiconductor. Typically, the exemplary recording is a magnetic tape, a magnetic disk, an optical disk, a magneto-optical disk, a flash memory, a solid state drive, or the like.

<Exemplary Ophthalmic Information Processing System>

The ophthalmic information processing system will be described. Based on the fundus morphological data and the background information of a subject, the exemplary ophthalmic information processing system 1 shown in FIG. 1 executes optic nerve head shape classification of the subject. The optic nerve head shape classification is typically Nicolela's classification, but other classification methods may be used.

Figure 1:
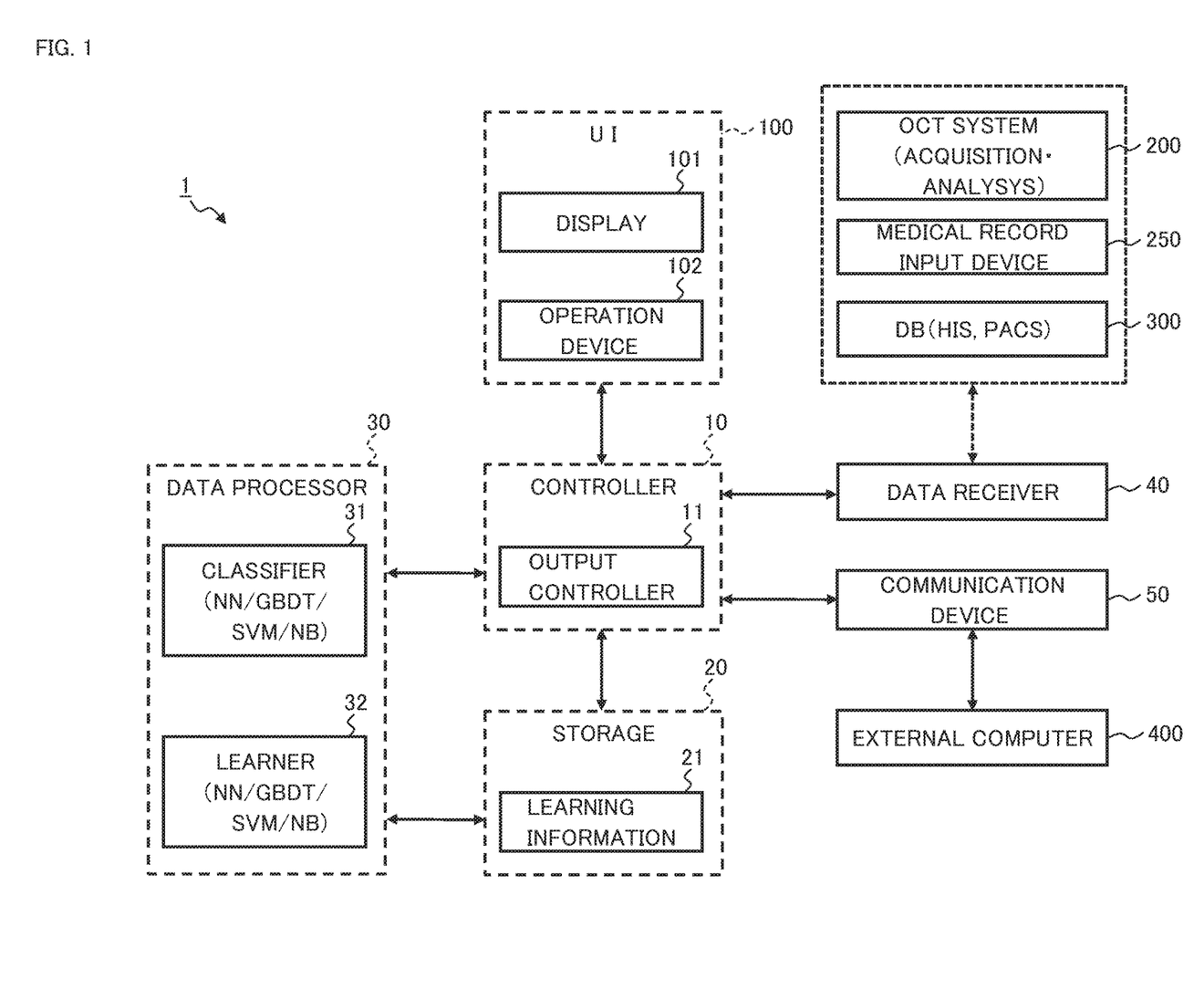
FIG. 1 is a schematic diagram illustrating an example of a configuration of an ophthalmic information processing system according to an exemplary embodiment.

The ophthalmic information processing system 1 includes the controller 10, the storage 20, the data processor 30, the data receiver 40, and the communication device 50. The user interface (UI) 100 may or may not be included in the ophthalmic information processing system 1. Elements included in the ophthalmic information processing system 1 are configured as a single apparatus or as two or more apparatuses. For example, the ophthalmic information processing system 1 includes a single computer with all the elements.

As an example of a configuration in which the ophthalmic information processing system 1 includes two or more apparatuses, provided are a computer including the controller 10, another computer including the storage 20, and another computer including the data processor 30. In an alternative example, the ophthalmic information processing system 1 includes a computer having any two of the controller 10, the storage 20, and the data processor 30, and another computer having the other one. The communication configuration between different computers may include wired communication and/or wireless communication and may include a dedicated line and/or a public line. The communication configuration between different computers may include at least one of a local area network (LAN), a wide area network (WAN), a short distance communication, and the Internet.

In the present embodiment, a computer executes various kinds of processes. The computer may be configured to function as an artificial intelligence engine. The computer includes one or more processors. A processor means a circuit such as a central processing unit (CPU), a graphics processing unit (GPU), an application specific integrated circuit (ASIC), a programmable logic device (e.g., a simple programmable logic device (SPLD), a complex programmable logic device (CPLD), a field programmable gate array (FPGA)). The processor realizes a desired function by reading out and executing a program stored in a storage device (a memory circuit), for example.

The processor can control the storage device and an output device. The storage device may be included in the computer or may be placed outside the computer. The same applies to the output device.

The ophthalmic information processing system 1 may include at least any one of the OCT system 200, the medical record input device 250, and the database (DB) 300. The OCT system 200 and the medical record input device 250 are connected to the database (DB) 300 via a network such as an in-hospital LAN.

<OCT System 200>

The OCT system 200 may have a data acquisition function to acquire data on the subject's eye (the fundus thereof) using optical coherence tomography (OCT). The data acquisition function is realized by, for example, a known Fourier domain OCT (also called frequency domain OCT) technique. As with the conventional Fourier domain OCT, the configuration that realizes the data acquisition function (i.e., OCT apparatus) includes a light source, an interference optical system, a photodetector, and an OCT data construction processor.

In the case where spectral domain OCT technique is adopted, the OCT apparatus includes the following elements: a low coherence light source; an interference optical system configured to split low coherence light output from the low coherence light source into measurement light and reference light, and superpose the measurement light returning from the subject's eye on the reference light that has been traveled through a reference optical path; a spectrometer configured to decompose interference light generated by the interference optical system in a space-divisional manner (i.e., to perform spectral decomposition of the interference light), and detect spectral data; and an OCT data construction processor configured to construct OCT image data by applying signal processing such as Fourier transform to signals output from the spectrometer.

In the case where swept source OCT technique is adopted, the OCT apparatus includes the following elements: a wavelength tunable light source; an interference optical system configured to split light sequentially output in a time-divisional manner from the wavelength-variable light source into measurement light and reference light, and superpose the measurement light returning from the subject's eye on the reference light that has been traveled through a reference optical path; a photodetector (e.g., a balanced photodiode) configured to detect interference light generated by the interference optical system; a data acquisition system (DAQ or DAS for short) configured to acquire signals output from the photodetector; and an OCT data construction processor configured to construct OCT image data by applying signal processing such as Fourier transform to spectral data acquired by the data acquisition system.

The OCT system 200 may have an analysis function for analyzing OCT image data. The analysis function is realized by an analysis processor configured to analyze fundus data acquired using OCT (i.e., OCT image data) to generate fundus morphological data. The analysis processor generates fundus morphological data for part or all of one or more types of parameters selected in advance by a computer or an expert, for example. The analysis processor may be configured to generate fundus morphological data for parameters other than those of the types selected in advance by the computer or the expert. The analysis processing executed by the analysis processor includes known processing used in the field of ophthalmology (more widely in the medical field, and even more widely in arbitrary fields).

<Medical Record Input Device 250>

The medical record input device 250 is a computer used for creating an electronic medical record. Typically, the medical record input device 250 may include any of a computer terminal used by a doctor, a processor that reads medical record items from input data, and a data scanner that reads information written on paper.

<Database 300>

The database 300 manages various kinds of data. The database 300 includes, for example, a hospital information system (HIS for short) and a medical image management system (e.g., picture archiving and communication systems, or PACS for short). The hospital information system includes an electronic medical record system. Data acquired by the OCT system 200 or other data acquisition apparatuses (e.g., an examination apparatus, an imaging apparatus) is stored in the electronic medical record system or the medical image management system. An electronic medical record created using a computer such as the medical record input device 250 is stored in the electronic medical record system.

The database 300 may include a screening database configured to store data acquired by screening such as a medical test or medical check-up.

<Controller 10>

The controller 10 executes various kinds of control. For example, the controller 10 executes control of individual element of the ophthalmic information processing system 1 and interlocking control of two or more elements. Further, the controller 10 can control external devices placed outside the ophthalmic information processing system 1. For example, when the user interface 100 is not included in the ophthalmic information processing system 1, the controller 10 can control the user interface 100. The controller 10 includes a processor.

<Output Controller 11>

The output controller 11 controls various kinds of output devices. The output device(s) may be at least one of a display device, an audio output device, a printing device, a communication device, and a data writer, for example. That is, the output controller 11 may be configured to execute at least one of the following kinds of control: control of the display device for displaying information; control of the audio output device for outputting audio information; control of the printing device for printing information on paper; control of the communication device for transmitting information to an external device; and control of the data writer for recording information on a recording medium.

The display 101 shown in FIG. 1 corresponds to the display device. The communication device 50 corresponds to the communication device. Although not shown, one or more of the audio output device, the printing device, and the data writer may be provided. Note that other types of output devices may be provided.

<Storage 20>

The storage 20 stores various kinds of data. Examples of data stored in the storage 20 include data received from outside by the data receiver 40. Typically, the storage 20 stores the fundus morphological data and the background data. The storage 20 includes, for example, at least one of a semiconductor storage device, a magnetic storage device, an optical storage device, and a magneto-optical storage device.

<Learning Information 21>

In the storage 20, the learning information 21 is stored in advance. The learning information 21 is referred to in the optic nerve head shape classification. The classification processing is executed by an arbitrary processor and is typically executed using an artificial intelligence technique. Also, the artificial intelligence technique of the same type as the classification processing is applied to learning.

Learning is executed using arbitrary machine learning techniques. As with known techniques, machine learning of the present embodiment analyzes prepared sample data sets to extract regularity, rules, knowledge representation and reasoning, judgment criteria, etc., and refines algorithms.

Machine learning algorithms are arbitrary, and typically, supervised learning can be employed. However, any type of technique such as unsupervised learning, semi supervised learning, reinforcement learning, transduction, multi-task learning, etc. may be adopted.

In the present embodiment, machine learning is executed by the learner 32 placed in the data processor 30. On the other hand, machine learning can be executed by a computer (i.e., a learner) placed outside the ophthalmic information processing system 1. The learner 32 (or an external learner) generates a classification model by executing machine learning based on a predetermined sample data set using a predetermined artificial intelligence technique. The classification model generated is included in the learning information 21.

In the present embodiment, any of artificial intelligence techniques among a neural network (NN), a gradient boosting decision tree (GBDT), a support vector machine (SVM), and Bayes (e.g., naive Bayes (NB)) is utilized. It is also possible to utilize other artificial intelligence techniques. In the present embodiment, a parameter of a type corresponding to an artificial intelligence technique adopted is used for learning.

In the case where the neural network is used for the optic nerve head shape classification, (at least one of) the following parameters are referred to for the classification as parameters of the fundus morphological data: cupping area, average cupping depth, maximum cupping depth, nasal rim-to-disc area ratio, horizontal disc angle, superior nasal circumpapillary retinal nerve fiber layer average thickness, and superior circumpapillary retinal nerve fiber layer average thickness. Further, (at least one of the parameters among) age and spherical equivalent are referred to for the classification as parameters of the background data. In addition, parameters of the same type as the parameters for the classification are used for learning. Instead of spherical equivalent, information equivalent or similar to it can be used. For example, it is possible to determine a parameter that can substitute for spherical equivalent from the axial length, aberration or the like of the subject's eye and include the determined parameter into the background data.

In the case where the gradient boosting decision tree is used for the optic nerve head shape classification, (at least one of) the following parameters are referred to for the classification as parameters of the fundus morphological data: horizontal disc angle, nasal rim-to-disc area ratio, average cupping depth, cup-to-disc area ratio, and superior nasal circumpapillary retinal nerve fiber layer average thickness. Further, (at least one of the parameters among) age and spherical equivalent are referred to for the classification as parameters of the background data. In addition, parameters of the same type as the parameters for the classification are used for learning.

In the case where the support vector machine is used for the optic nerve head shape classification, (at least one of) the following parameters are referred to for the classification as parameters of the fundus morphological data: horizontal disc diameter, average cupping depth, nasal rim-to-disc area ratio, horizontal disc angle, superior nasal circumpapillary retinal nerve fiber layer average thickness, superior circumpapillary retinal nerve fiber layer average thickness, and disc retinal pigment epithelium height difference. Further, (at least one of the parameters among) age and spherical equivalent are referred to for the classification as parameters of the background data. In addition, parameters of the same type as the parameters for the classification are used for learning.

In the case where the naive Bayes is used for the optic nerve head shape classification, (at least one of) the following parameters are referred to for the classification as parameters of the fundus morphological data: superior circumpapillary retinal nerve fiber layer average thickness, nasal rim-to-disc area ratio, horizontal disc angle, and average cupping depth. Further, (at least one of the parameters among) age and spherical equivalent are referred to for the classification as parameters of the background data. In addition, parameters of the same type as the parameters for the classification are used for learning.

Selection of the parameters (i.e., the fundus morphological data and the background data) according to the type of artificial intelligence technique will be described. the inventors performed machine learning using each of a neural network learner, a gradient boosting decision tree learner, a support vector machine learner, and a naive Bayes learner, on the basis of a sample data set relating to N eyes of patients (also called sample eyes) with open-angle glaucoma diagnosed by doctors based on interpretation and analysis of OCT images, color fundus images, and patient background data.

The sample data set includes at least fundus morphological data obtained by analyzing three dimensional OCT data. For example, segmentation is applied to three dimensional OCT data, the outer edge (or, contour or outline) of the optic nerve head and the outer edge of the cupping are detected from the result of the segmentation, and fundus morphological data is generated from the results of the detections. Examples of fundus morphological data generated in such a way include optic nerve head shape parameters and circumpapillary retinal nerve fiber layer thickness. Furthermore, the sample data set may include blood flow dynamics data obtained by laser speckle flowgraphy (LSFG). The laser speckle flowgraphy is a modality for imaging blood flow utilizing laser scattering.

Using swept source OCT, the inventors prepared 22 types of optic nerve head shape parameters and 26 types of circumpapillary retinal nerve fiber layer thickness (cpRNFLT) parameters. Further, 36 types of blood flow parameters were prepared using laser speckle flowgraphy. In addition, 7 types of background parameters were prepared from the patient's medical record.

A list of the parameters (feature amounts) considered by the inventors is shown in FIG. 2. In the list, Nos. 1 to 7 are seven types of background parameters, Nos. 8 to 29 are 22 types of optic nerve head shape parameters, Nos. 30 to 55 are 26 types of circumpapillary retinal nerve fiber layer thickness parameters, and Nos. 56 to 91 are 36 types of blood flow parameters.

Furthermore, the inventors divided N sample eyes into N1 pieces of training data and N2 pieces of test data in a random manner, created a classification model by means of feature selection and machine learning based on the training data, and confirmed the performance of the classification model based on the test data.

The inventors used the result of Nicolela's classification for the N sample eyes determined by doctors as training data. Further, supervised learning was performed using each of the neural network, the gradient boosting decision tree, the support vector machine, and the naive Bayes to construct a classification model, and the performance of each classification model thus constructed was evaluated. Note that the feature selection was performed to select an optimal parameter(s) out of 91 parameters (i.e., 91 feature amounts).

In the case where the gradient boosting decision tree was adopted, the embedded feature selection method was employed as a feature selection method, and 10-fold cross-validation was employed as a performance evaluation index. In the case where the neural network, the support vector machine, or the naive Bayes was adopted, the feature selection was performed using the combination of: the minimum redundancy maximum relevance (mRMR for short) which is one of the filter type feature selection methods; and the genetic algorithm (GA for short) which is one of the wrapper type feature selection methods. In addition, the performance evaluation was performed using 10-fold cross-validation.

As the result of the above classification evaluation, accuracy rates of 80% or more were obtained for all of the neural network case, the gradient boosting decision tree case, the support vector machine case, and the naive Bayes case. Note that the neural network case exhibited the highest accuracy rate among the four cases.

Furthermore, the following parameters were selected as the optimal parameter types in the neural network case: cupping area (No. 9), average cupping depth (No. 18), maximum cupping depth (No. 17), nasal rim-to-disc area ratio (No. 22), horizontal disc angle (No. 26), superior nasal circumpapillary retinal nerve fiber layer average thickness (No. 38), superior circumpapillary retinal nerve fiber layer average thickness (No. 32), age (No. 2), and spherical equivalent (No. 3).

In the gradient boosting decision tree case, the following parameters were selected as the optimal parameter types: horizontal disc angle (No. 26), nasal rim-to-disc area ratio (No. 22), average cupping depth (No. 18), cup-to-disc area ratio (No. 15), superior nasal circumpapillary retinal nerve fiber layer average thickness (No. 38), age (No. 2), and spherical equivalent (No. 3).

In the support vector machine case, the following parameters were selected as the optimal parameter types: horizontal disc diameter (No. 12), average cupping depth (No. 18), nasal rim-to-disc area ratio (No. 22), horizontal disc angle (No. 26), superior nasal circumpapillary retinal nerve fiber layer average thickness (No. 38), superior circumpapillary retinal nerve fiber layer average thickness (No. 32), disc retinal pigment epithelium height difference (No. 28), age (No. 2), and spherical equivalent (No. 3).

In naive Bayes case, the following parameters were selected as the optimal parameter types: superior circumpapillary retinal nerve fiber layer average thickness (No. 32), nasal rim-to-disc area ratio (No. 22), horizontal disc angle (No. 26), average cupping depth (No. 18), age (No. 2), and spherical equivalent (No. 3).

As can be seen from the above, several types of fundus morphological data based on OCT and two types of background data (namely, age and spherical equivalent) were selected as optimal parameter types in any of the neural network case, the gradient boosting decision tree case, the support vector machine case, and the naive Bayes case. The ophthalmic information processing system 1 is constructed on the basis of such research results.

<Data Receiver 40>

The data receiver 40 receives fundus morphological data and background data of the subject. In the present embodiment, for example, the fundus morphological data is generated by the OCT system 200 and stored in the database 300 (e.g., electronic medical record system, PACS). In addition, the background data is generated using the medical record input device 250 and stored in the database 300 (e.g., electronic medical record system), for example.

The data receiver 40 receives the fundus morphological data and the background data from the database 300. For example, when a doctor designates one or more patients, data of each designated patient is input to the ophthalmic information processing system 1 via the data receiver 40. Alternatively, when a patient ID or the like is input to the ophthalmic information processing system 1, the controller 10 acquires data from the database 300 via the data receiver 40 with the patient ID or identification information associated with the patient ID as a search query.

<Communication Device 50>

The communication device 50 executes transmission of data to another computer (i.e., the external computer 400) and reception of data from the external computer 400. The communication device 50 includes known communication equipment conformable to a communication system for communicating with the external computer 400. Note that the data receiver 40 and the communication device 50 may be configured as a single device.

<Data Processor 30>

The data processor 30 executes various kinds of data processing. The data processor 30 includes the classifier 31 and the learner 32.

<Classifier 31>

The classifier 31 is an example of a processor that executes optic nerve head shape classification based on the fundus morphological data and the background data received by the data receiver 40. The classifier 31 of the present embodiment includes an artificial intelligence engine, and executes optic nerve head shape classification based on the learning information 21 stored in the storage 20 and the fundus morphological data and the background data received by the data receiver 40.

In the case where an artificial intelligence engine utilizing neural network is employed, the following parameters are used, for example, as fundus morphological data: cupping area, average cupping depth, maximum cupping depth, nasal rim-to-disc area ratio, horizontal disc angle, superior nasal circumpapillary retinal nerve fiber layer average thickness, and superior circumpapillary retinal nerve fiber layer average thickness. In addition, age and spherical equivalent are used as background data, for example. The learning information 21 includes in advance a classification model generated by learning based on the same types of data group as the fundus morphological data and the same types of data group as the background data. Generation of the classification model is executed by the learner 32 utilizing neural network. The classifier 31 utilizing neural network (i.e., a neural network classifier) determines confidence for each of the four types of Nicolela's classification based on the classification model as well as the fundus morphological data and the background data of the subject. Note that instead of determining the confidence for all of the four types, confidence may be determined only for any one, two, or three out of the four types.

In the case where an artificial intelligence engine utilizing gradient boosting decision tree is employed, the following parameters are used, for example, as fundus morphological data: horizontal disc angle, nasal rim-to-disc area ratio, average cupping depth, cup-to-disc area ratio, and superior nasal circumpapillary retinal nerve fiber layer average thickness. In addition, age and spherical equivalent are used as background data, for example. The learning information 21 includes in advance a classification model generated by learning based on the same types of data group as the fundus morphological data and the same types of data group as the background data. Generation of the classification model is executed by the learner 32 utilizing gradient boosting decision tree. The classifier 31 utilizing gradient boosting decision tree (i.e., a gradient boosting decision tree classifier) determines confidence for each of the four types of Nicolela's classification based on the classification model as well as the fundus morphological data and the background data of the subject. Note that instead of determining the confidence for all of the four types, confidence may be determined only for any one, two, or three out of the four types.

In the case where an artificial intelligence engine utilizing support vector machine is employed, the following parameters are used, for example, as fundus morphological data: horizontal disc diameter, average cupping depth, nasal rim-to-disc area ratio, horizontal disc angle, superior nasal circumpapillary retinal nerve fiber layer average thickness, superior circumpapillary retinal nerve fiber layer average thickness, and disc retinal pigment epithelium height difference. In addition, age and spherical equivalent are used as background data, for example. The learning information 21 includes in advance a classification model generated by learning based on the same types of data group as the fundus morphological data and the same types of data group as the background data. Generation of the classification model is executed by the learner 32 utilizing the support vector machine. The classifier 31 utilizing support vector machine (i.e., a support vector machine classifier) determines confidence for each of the four types of Nicolela's classification based on the classification model as well as the fundus morphological data and the background data of the subject. Note that instead of determining the confidence for all of the four types, confidence may be determined only for any one, two, or three out of the four types.

In the case where an artificial intelligence engine utilizing naive Bayes is employed, the following parameters are used, for example, as fundus morphological data: superior circumpapillary retinal nerve fiber layer average thickness, nasal rim-to-disc area ratio, horizontal disc angle, and average cupping depth. In addition, age and spherical equivalent are used as background data, for example. The learning information 21 includes in advance a classification model generated by learning based on the same types of data group as the fundus morphological data and the same types of data group as the background data. Generation of the classification model is executed by the learner 32 utilizing naive Bayes. The classifier 31 utilizing naive Bayes (i.e., a naive Bayes classifier) determines confidence for each of the four types of Nicolela's classification based on the classification model as well as the fundus morphological data and the background data of the subject. Note that instead of determining the confidence for all of the four types, confidence may be determined only for any one, two, or three out of the four types.

<Learner 32>

The learner 32 generates the learning information 21 by executing machine learning based on the same types of data group as the fundus morphological data and the same types of data group as the background data.

In the case where the artificial intelligence engine utilizing neural network is employed, the learner 32 generates the learning information 21 (i.e., a classification model) by executing machine learning according to neural network based on, for example, the followings: cupping area, average cupping depth, maximum cupping depth, nasal rim-to-disc area ratio, horizontal disc angle, superior nasal circumpapillary retinal nerve fiber layer average thickness, superior circumpapillary retinal nerve fiber layer average thickness, age and spherical equivalent. The neural network classifier 31 executes Nicolela's classification based on the classification model generated.

In the case where the artificial intelligence engine utilizing gradient boosting decision tree is employed, the learner 32 generates the learning information 21 (i.e., a classification model) by executing machine learning according to gradient boosting decision tree based on, for example, the followings: horizontal disc angle, nasal rim-to-disc area ratio, average cupping depth, cup-to-disc area ratio, superior nasal circumpapillary retinal nerve fiber layer average thickness, age and spherical equivalent. The gradient boosting decision tree classifier 31 executes Nicolela's classification based on the classification model generated.

In the case where the artificial intelligence engine utilizing support vector machine is employed, the learner 32 generates the learning information 21 (i.e., a classification model) by executing machine learning according to support vector machine based on, for example, the followings: horizontal disc diameter, average cupping depth, nasal rim-to-disc area ratio, horizontal disc angle, superior nasal circumpapillary retinal nerve fiber layer average thickness, superior circumpapillary retinal nerve fiber layer average thickness, disc retinal pigment epithelium height difference, age and spherical equivalent. The support vector machine classifier 31 executes Nicolela's classification based on the classification model generated.

In the case where the artificial intelligence engine utilizing naive Bayes is employed, the learner 32 generates the learning information 21 (i.e., a classification model) by executing machine learning according to naive Bayes based on, for example, the followings: superior circumpapillary retinal nerve fiber layer average thickness, nasal rim-to-disc area ratio, horizontal disc angle, average cupping depth, age and spherical equivalent. The naive Bayes classifier 31 executes Nicolela's classification based on the classification model generated.

<User Interface 100>

The user interface 100 includes the display 101 and the operation device 102. The display 101 includes a display device such as a flat panel display. The operation device 102 includes operation devices such as a mouse, a keyboard, a track pad, buttons, keys, a joystick, an operation panel, and the like.

The display 101 and the operation device 102 need not be configured as separate devices. It is possible to use a single device in which a display function and an operation function are integrated like a touch panel. In that case, the operation device 102 includes the touch panel and a computer program. The content of an operation performed using the operation device 102 is input to the controller 10 as an electric signal. In addition, operation and information input may be performed using a graphical user interface (GUI for short) displayed on the display 101 and the operation device 102.

<Usage Mode>

Figure 3:
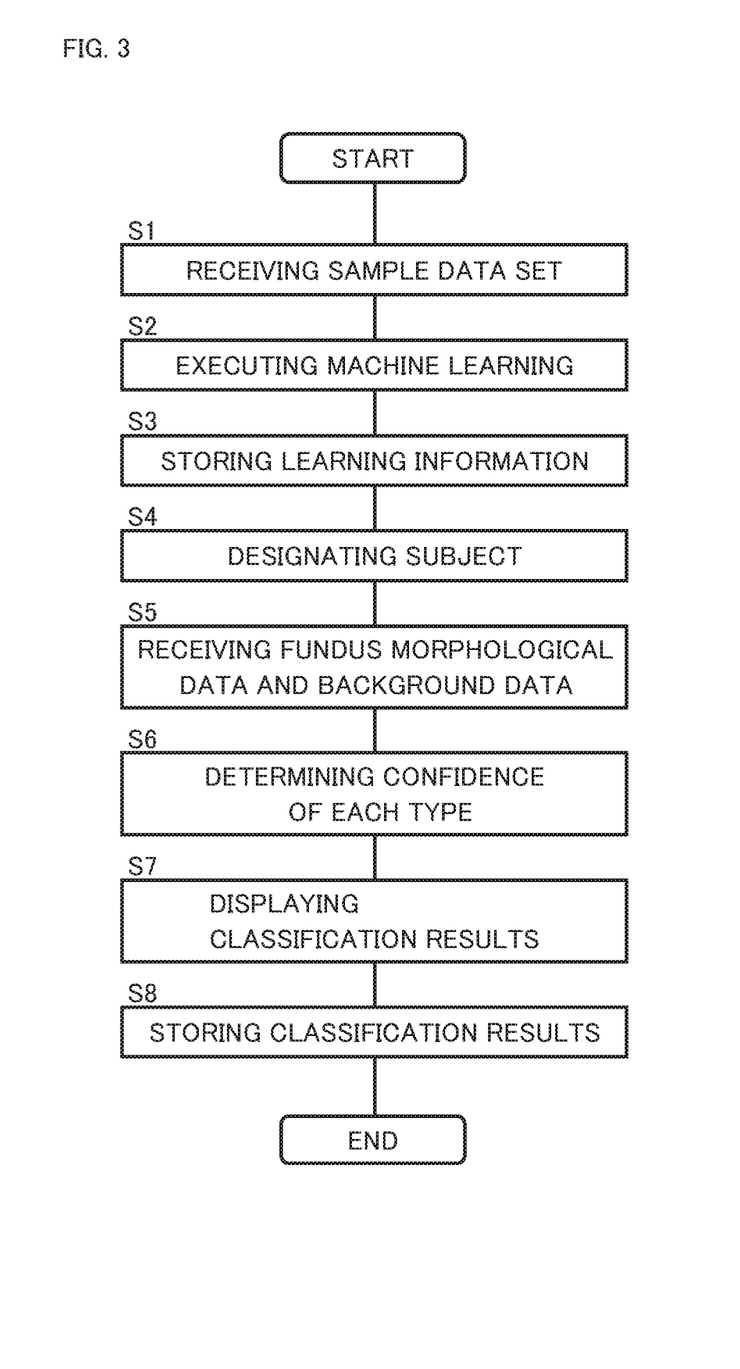
FIG. 3 is a flowchart representing an example of a usage mode that can be implemented using the ophthalmic information processing system according to the exemplary embodiment.

The usage modes that can be implemented by the ophthalmic information processing system 1 will be described. FIG. 3 shows an example of the usage mode. In the present exemplary usage mode, the optic nerve head shape classification (i.e., Nicolela's classification) for a specific subject is executed following the generation of the learning information 21. However, the learning information generation and the classification need not be performed consecutively. For example, the learning information 21 may be updated every predetermined period.

(S1: Receiving Sample Data Set)

First, the data receiver 40 of the ophthalmic information processing system 1 receives, via the network, a sample data set (i.e., fundus morphological data group and patient background data) stored in the database 300.

For example, the controller 10 controls the data receiver 40 to transmit a transmission request of the sample data set, information indicating the types of data to be processed, and the like to the database 300. As a specific example, when neural network is adopted, the controller 10 controls the data receiver 40 to transmit, to the database 300, a transmission request of the sample data set (including a target disease name), and information indicating the data types corresponding to the neural network, namely, cupping area, average cupping depth, maximum cupping depth, nasal rim-to-disc area ratio, horizontal disc angle, superior nasal circumpapillary retinal nerve fiber layer average thickness, superior circumpapillary retinal nerve fiber layer average thickness, age and spherical equivalent.

For example, the database 300 specifies subjects (i.e., patients) corresponding to the target disease name (e.g., open-angle glaucoma) by referring to electronic medical records. Subsequently, the database 300 obtains ages and spherical equivalent values from the electronic medical records of the patients specified. In addition, the database 300 obtains the following types of data from the electronic medical records of the patients specified: cupping area values, average cupping depth values, maximum cupping depth values, nasal rim-to-disc area ratio values, horizontal disc angle values, superior nasal circumpapillary retinal nerve fiber layer average thickness values, and superior circumpapillary retinal nerve fiber layer average thickness values.

In the case where target data is not stored in the database 300, the data can be generated. The data generation may be executed by the ophthalmic information processing system 1 or by a device other than the ophthalmic information processing system 1.

For example, in the case where one or more types of the fundus morphological data does not exist, the database 300 sends OCT data of a concerned subject stored in the database 300 (e.g., PACS) to the OCT system 200 together with an analysis request. The analysis request includes an analysis type information. The OCT system 200 generates target data by applying analysis processing corresponding to the analysis request to the OCT data. Then, the OCT system 200 sends the generated target data to the database 300. The database 300 can send fundus morphological data including the generated target data to the ophthalmic information processing system 1. As another example, in the case where a spherical equivalent value is not recorded in an electronic medical record, the spherical power value and the astigmatic power value recorded in the electronic medical record can be used to calculate the spherical equivalent value.

When the target data is generated by the ophthalmic information processing system 1, the database 300 sends to the ophthalmic information processing system 1 data required for obtaining the target data. Here, the types of data required for obtaining the target data are determined in advance. The data processor 30 generates the target data based on the data input from the database 300.

(S2: Executing Machine Learning)

The learner 32 (or a learner placed outside the ophthalmic information processing system 1) generates the learning information 21 (i.e., a classification model) by executing machine learning based on the sample data set received in step S1.

(S3: Storing Learning Information)

The controller 10 stores the learning information 21 generated in step S2 in the storage 20. When the learning information generated in the past has been stored in the storage 20, it is possible to update the past learning information with new learning information. Alternatively, a plurality of pieces of learning information may be accumulated together with information indicating their generation dates and times.

(S4: Designating Subject)

A user such as a doctor, the ophthalmic information processing system 1, or the external computer 400 designates one or more subjects.

When the user designates a subject(s), the ophthalmic information processing system 1 or the external computer 400 displays a screen for subject designation on the display device. The user uses the operation device to designate one or more subjects. At this time, for example, a group of patients who have undergone medical check-up may be designated at a time. Also, a configuration may be adopted in which subjects suspected of suffering from a specific disease can be designated (at a time).

When the ophthalmic information processing system 1 or the external computer 400 designates a subject(s), it is possible to designate a subject(s) based on date and time, the name of a specific disease, the presence or absence of suspicion of a specific disease, the type of screening, or the like.

(S5: Receiving Fundus Morphological Data and Background Data)

For each of the one or more subjects designated in step S4, the data receiver 40 of the ophthalmic information processing system 1 receives the fundus morphological data group and the patient background data stored in the database 300 through the network.

Here, the transmission request, information indicating the type of data to be transmitted, the operation of the database 300, and the operation of the ophthalmic information processing system 1 may be the same as those in step S1.

(S6: Determining Confidence of Each Type)

Based on the fundus morphological data group and the patient background data received in step S5 as well as the learning information 21 stored in the storage 20 in step S3, the classifier 31 executes Nicolela's classification on each eye of each subject. With this, for example, the confidence is determined for each of the four types of Nicolela's classification.

(S7: Displaying Classification Results)

The output controller 11 displays the confidence of each type determined in step S6 on the display 101.

Figure 4:
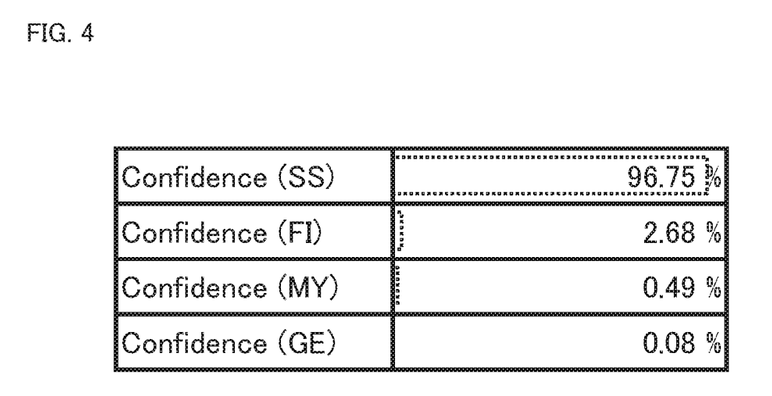
FIG. 4 is an example of a result of classification that can be displayed by the ophthalmic information processing system according to the exemplary embodiment.

An example of the display mode of the confidence is shown in FIG. 4. In the display mode of the present example, the confidences for the four types of Nicolela's classification are listed from the top in descending order of their values. The example shown in FIG. 4 includes table information in which the followings are listed from the top: the confidence of the senile sclerotic (SS) type, "Confidence (SS)"; the confidence of the focal ischemia (FI) type, "Confidence (FI)"; the confidence of the myopic (MY) type, "Confidence (MY)"; and the confidence of the generalized enlargement (GE) type, "Confidence (GE)". In addition, bar graphs (indicated by dotted lines) showing the magnitudes of the confidences are presented together with the numerical values of the confidences.

According to such a display mode of classification results, it is possible to comprehend the confidences of all types in Nicolela's classification, and further to easily see the relative difference between the magnitudes of the types. Therefore, it is easy to know to which type of Nicolela's classification the shape of the optic nerve head of the subject's eye belongs. Also, it is easy to know the degree of reliability of the classification executed by the ophthalmic information processing system 1.

(S8: Storing Classification Results)

The controller 10 can store the confidence of each type determined in step S6 and the information displayed in FIG. 7 in the storage 20. Further, the controller 10 can transmit such classification results to the database 300 and/or the external computer 400. The database 300 and/or the external computer 400 can store the classification result received from the ophthalmic information processing system 1.

<Actions and Effects>

The actions and effects of the exemplary embodiment described above will be described.

The ophthalmic information processing system according to the exemplary embodiment includes a receiver and a processor. The receiver is configured to receive morphological data of an eye fundus of a subject and background data of the subject. The processor is configured to execute optic nerve head shape classification based on the morphological data and the background data received by the receiver.

In the ophthalmic information processing system 1 described above, the data receiver 40 corresponds to the receiver, and the classifier 31 corresponds to the processor. Also, the ophthalmic information processing system 1 is configured to execute Nicolela's classification as the optic nerve head shape classification.

The ophthalmic information processing system according to the exemplary embodiment may further include a storage. In the present example, learning information is generated by learning based on the same type of data group as the morphological data used for the optic nerve head shape classification and based on the same type of data group as the background data. The storage stores the learning information in advance. The processor is configured to execute the optic nerve head shape classification based on the learning information stored in the storage as well as the morphological data and the background data received by the receiver.

In the above ophthalmic information processing system 1, the storage 20 corresponds to the storage and the learning information 21 corresponds to the learning information.

In the ophthalmic information processing system according to the exemplary embodiment, the morphological data may include at least one of cupping area, average cupping depth, maximum cupping depth, nasal rim-to-disc area ratio, horizontal disc angle, superior nasal circumpapillary retinal nerve fiber layer average thickness, and superior circumpapillary retinal nerve fiber layer average thickness. In addition, the background data may include at least one of age and spherical equivalent. Further, the learning information includes a classification model generated by learning using neural network. In addition, the processor includes a neural network classifier.

In the case where neural network is adopted in the above embodiment, typical morphological data in the ophthalmic information processing system 1 includes all of the cupping area, the average cupping depth, the maximum cupping depth, the nasal rim-to-disc area ratio, the horizontal disc angle, the superior nasal circumpapillary retinal nerve fiber layer average thickness, and the superior circumpapillary retinal nerve fiber layer average thickness. In addition, typical background data includes both the age and the spherical equivalent. The classifier 31 corresponds to the neural network classifier.

In the ophthalmic information processing system according to the exemplary embodiment, the morphological data includes at least one of horizontal disc angle, nasal rim-to-disc area ratio, average cupping depth, cup-to-disc area ratio, and superior nasal circumpapillary retinal nerve fiber layer average thickness. Also, the background data includes at least one of age and spherical equivalent. Further, the learning information includes a classification model generated by learning using gradient boosting decision tree. In addition, the processor includes a gradient boosting decision tree classifier.

In the case where gradient boosting decision tree is adopted in the above embodiment, typical morphological data in the ophthalmic information processing system 1 includes all of the horizontal disc angle, the nasal rim-to-disc area ratio, the average cupping depth, the cupping disc area ratio, and the superior nasal circumpapillary retinal nerve fiber layer average thickness. In addition, typical background data includes both the age and the spherical equivalent. The classifier 31 corresponds to the gradient boosting decision tree classifier.

In the ophthalmic information processing system according to the exemplary embodiment, the morphological data includes at least one of horizontal disc diameter, average cupping depth, nasal rim-to-disc area ratio, horizontal disc angle, superior nasal circumpapillary retinal nerve fiber layer average thickness, superior circumpapillary retinal nerve fiber layer average thickness, and disc retinal pigment epithelium height difference. Also, the background data includes at least one of age and spherical equivalent. Further, the learning information includes a classification model generated by learning using support vector machine. In addition, the processor includes a support vector machine classifier.

In the case where support vector machine is adopted in the above embodiment, typical morphological data in the ophthalmic information processing system 1 includes all of the horizontal disc diameter, the average cupping depth, the nasal rim-to-disc area ratio, the horizontal disc angle, the superior nasal circumpapillary retinal nerve fiber layer average thickness, the superior circumpapillary retinal nerve fiber layer average thickness, and the disc retinal pigment epithelium height difference. In addition, typical background data includes both the age and the spherical equivalent. The classifier 31 corresponds to the support vector machine classifier.

In the ophthalmic information processing system according to the exemplary embodiment, the morphological data includes at least one of superior circumpapillary retinal nerve fiber layer average thickness, nasal rim-to-disc area ratio, horizontal disc angle, and average cupping depth. Also, the background data includes at least one of age and spherical equivalent. Further, the learning information includes a classification model generated by learning using (the theorem of) Bayes (e.g., naive Bayes). In addition, the processor includes a Bayes classifier.

In the case where Bayes is adopted in the above embodiment, typical morphological data in the ophthalmic information processing system 1 includes all of the superior circumpapillary retinal nerve fiber layer average thickness, the nasal rim-to-disc area ratio, the horizontal disc angle, and the average cupping depth. In addition, typical background data includes both the age and the spherical equivalent. The classifier 31 corresponds to the Bayes classifier.

The ophthalmic information processing system according to the exemplary embodiment may further include a learner. The learner is configured to execute learning based on the same type of data group as the morphological data and the same type of data group as the background data, to generate the learning information.

In the above ophthalmic information processing system 1, the learner 32 corresponds to the learner.

In the ophthalmic information processing system according to the exemplary embodiment, the processor may be configured to execute the optic nerve head shape classification to determine confidence for each of one or more types of the shape of optic nerve head. In addition, the ophthalmic information processing system according to the exemplary embodiment may further include a display controller. The display controller is configured to display the confidence for the one or more types, on a display device.

In the typical usage mode of the above ophthalmic information processing system 1, the confidences of all four types in Nicolela's classification are determined. In addition, in the above ophthalmic information processing system 1, the output controller 11 corresponds to the display controller, and the display 101 corresponds to the display device. It should be noted that the display device may be included in the ophthalmic information processing system or it may be placed outside the ophthalmic information processing system.

In the ophthalmic information processing system according to the exemplary embodiment, at least part of the morphological data, which is used for the optic the nerve head shape classification, may be generated by analyzing data of the eye fundus acquired using optical coherence tomography.

In the above ophthalmic information processing system 1, OCT scan is applied to a three dimensional region of the eye fundus. In the analysis, the layer structure of the eye fundus is specified by applying segmentation to the three dimensional OCT data acquired through the OCT scan. On the basis of the layer structure specified, a disc area (disc for short), cupping area (cup for short), a rim area (rim for short), a circumpapillary retinal nerve fiber layer, etc. are specified. Then, the area and/or the diameter of the disc area, the area and/or the diameter of the cupping area, the area and/or the diameter of the rim area, etc. are calculated. Further, the area ratio and/or the diameter ratio of any two of the disc area, the supping area, and the rim area are calculated. In addition, the depth of the cupping area, the gradient (or angle) of the disc area, etc. are calculated. Further, the layer thickness values of the circumpapillary retinal nerve fiber layer in a plurality of sectors are calculated, and the feature amounts are calculated based on the calculated layer thickness values for these sectors.

The ophthalmic information processing system according to the exemplary embodiment may further include an analysis processor. The analysis processor is configured to analyze data of an eye fundus acquired using optical coherence tomography, to generate morphological data.

In the above ophthalmic information processing system 1, at least one of the OCT system 200 (the analysis function thereof), the data processor 30, and the external computer 400 functions as the analysis processor.

The ophthalmic information processing system according to the exemplary embodiment may further include an optical coherence tomography apparatus configured to acquire data of an eye fundus using optical coherence tomography.

In the above ophthalmic information processing system 1, the OCT system 200 (the data aquisition function thereof) functions as the optical coherence tomography apparatus.

In the ophthalmic information processing system according to the exemplary embodiment, the receiver may be configured to receive at least part of the background data directly or indirectly from an electronic medical record system.

In the above ophthalmic information processing system 1, the database 300 includes the electronic medical record system, and age and spherical equivalent are acquired from the electronic medical record system.

The ophthalmic information processing method according to the exemplary embodiment is implemented using a computer. The computer receives morphological data of an eye fundus of a subject and background data of the subject. In addition, the computer executes optic nerve head shape classification based on the morphological data and the background data received.

The program according to the exemplary embodiment is a program that causes a computer to execute the ophthalmic information processing method according to the exemplary embodiment.

The recording medium according to the exemplary embodiment is a non-transitory computer-readable recording medium in which the program according to the exemplary embodiment is recorded.

The exemplary embodiments configured as above enable automatic classification of optic nerve head shape in place of the conventional optic nerve head shape classifications relying on the subjectivity of doctors. Consequently, it becomes possible to widely provide, for example, screening for a disease with a relatively high prevalence rate or a disease for which early detection is important. Further, in medical treatment for diseases such as glaucoma, it becomes possible to easily determine a treatment policy according to the shape of the optic nerve head.

In addition, according to the exemplary embodiments, optic nerve head shape parameters can be quantified with analysis of data acquired using optical coherence tomography. Therefore, as compared with the conventional cases of referring to fundus images obtained by retinal cameras or SLOs, quantification of the optic nerve head shape parameters is easier, and the automation of the optic nerve head shape classification is further promoted.

Further, according to the exemplary embodiments, a parameter(s) having high contribution to the optic nerve head shape classification can be selected and referred to. Therefore, the classification can be carried out with favorable accuracy and precision without wastefully referring to a large amount of data.

As such, the exemplary embodiments can realize automatic execution of the optic nerve head shape classification with favorable accuracy and precision.

In addition, according to the exemplary embodiments capable of performing the feature selection described above, the optic nerve head shape classification can be automatically performed with favorable accuracy and precision without adopting a large-scale system.

Processes included in the ophthalmic information processing method and elements (e.g., configuration, operation) included in the ophthalmic information processing system according to embodiments are not limited to the above examples.

The embodiments described above are merely examples of the present invention. Those who intend to implement the present invention can apply any modification (e.g., omission, substitution, addition) within the scope of the gist of the present invention.

As an exemplary modification, a configuration can be employed in which the feature selection is not involved. For example, utilization of a learning algorithm such as random forest makes it possible to execute the optic nerve head shape classification without the feature selection.

As another exemplary modification, fundus images acquired using retinal cameras or SLOs may be utilized. For example, at least part of the morphological data can be generated by analyzing the fundus images acquired using retinal cameras and/or SLOs. Examples of morphological data that can be generated from fundus images acquired using retinal cameras and/or SLOs include disc area, cupping area, rim area, disc diameter, cupping diameter, and rim diameter.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic information processing system comprising:
    a receiver that receives morphological data of an eye fundus of a subject and background data of the subject; and
    a processor that executes optic nerve head shape classification, using an artificial intelligence-based classifier, based on the morphological data and the background data.

2. The ophthalmic information processing system of claim 1, further comprising a storage that pre-stores learning information generated by machine learning based on a same type of data group as the morphological data and a same type of data group as the background data,
    wherein the processor executes the optic nerve head shape classification based on the learning information, the morphological data and the background data.

3. The ophthalmic information processing system of claim 2, wherein
    the morphological data comprises at least one of cupping area, average cupping depth, maximum cupping depth, nasal rim-to-disc area ratio, horizontal disc angle, superior nasal circumpapillary retinal nerve fiber layer average thickness, and superior circumpapillary retinal nerve fiber layer average thickness,
    the background data comprises at least one of age and spherical equivalent,
    the learning information comprises a classification model generated by learning using an artificial neural network, and
    the processor comprises a neural network classifier.

4. The ophthalmic information processing system of claim 2, wherein
    the morphological data comprises at least one of horizontal disc angle, nasal rim-to-disc area ratio, average cupping depth, cup-to-disc area ratio, and superior nasal circumpapillary retinal nerve fiber layer average thickness,
    the background data comprises at least one of age and spherical equivalent,
    the learning information comprises a classification model generated by learning using a gradient boosting decision tree, and
    the processor comprises a gradient boosting decision tree classifier.

5. The ophthalmic information processing system of claim 2, wherein
    the morphological data comprises at least one of horizontal disc diameter, average cupping depth, nasal rim-to-disc area ratio, horizontal disc angle, superior nasal circumpapillary retinal nerve fiber layer average thickness, superior circumpapillary retinal nerve fiber layer average thickness, and disc retinal pigment epithelium height difference,
    the background data comprises at least one of age and spherical equivalent,
    the learning information comprises a classification model generated by learning using a support vector machine, and
    the processor comprises a support vector machine classifier.

6. The ophthalmic information processing system of claim 2, wherein
    the morphological data comprises at least one of superior circumpapillary retinal nerve fiber layer average thickness, nasal rim-to-disc area ratio, horizontal disc angle, and average cupping depth,
    the background data comprises at least one of age and spherical equivalent,
    the learning information comprises a classification model generated by learning using Bayes, and
    the processor comprises a Bayes classifier.

7. The ophthalmic information processing system of claim 2, further comprising a learner that executes machine learning based on the same type of data group as the morphological data and the same type of data group as the background data to generate the learning information.

8. The ophthalmic information processing system of claim 1, wherein
    the processor executes the optic nerve head shape classification to determine confidence for each of one or more types of optic nerve head shape, and
    the system further comprising a display controller that displays the confidence of the one or more types on a display device.

9. The ophthalmic information processing system of claim 1, wherein at least part of the morphological data is generated by analyzing data of the eye fundus acquired using optical coherence tomography.

10. The ophthalmic information processing system of claim 9, further comprising an analysis processor that analyzes data of the eye fundus acquired using optical coherence tomography to generate morphological data.

11. The ophthalmic information processing system of claim 10, further comprising an optical coherence tomography apparatus that acquires data of the eye fundus using optical coherence tomography.

12. The ophthalmic information processing system of claim 1, wherein the receiver receives at least part of the background data directly or indirectly from an electronic medical record system.

13. A method of processing ophthalmic information executed by a computer, the method comprising:
    receiving morphological data of an eye fundus of a subject and background data of the subject; and
    executing optical nerve head shape classification, using an artificial intelligence-based classifier, based on the morphological data and the background data.

14. A non-transitory computer-readable recording medium storing a program that causes a computer to execute the ophthalmic information processing method of claim 13.

* * * * *

UNITED STATES PATENT AND TRADEMARK OFFICE
CERTIFICATE OF CORRECTION

PATENT NO. : 10,765,316 B2
APPLICATION NO. : 15/925922
DATED : September 8, 2020
INVENTOR(S) : Guangzhou An et al.

It is certified that error appears in the above-identified patent and that said Letters Patent is hereby corrected as shown below:

On the Title Page

At Item (72), the Inventors information:
"Masahiro AKIBA, Toda (JP)" should read --Masahiro AKIBA, Toda-shi (JP)--;
Toru NAKAZAWA, "Sendai (JP)" should read --Sendai-shi (JP)--;
Kazuko OMODAKA, "Sendai (JP)" should read --Sendai-shi (JP)--; and
Hideo YOKOTA, "Wako (JP)" should read --Wako-shi (JP)--.

Signed and Sealed this
Seventeenth Day of November, 2020

Andrei Iancu
*Director of the United States Patent and Trademark Office*